United States Patent [19]

Usmar et al.

[11] Patent Number: 4,596,146
[45] Date of Patent: Jun. 24, 1986

[54] MOUNTING

[75] Inventors: Ronald A. Usmar, Didcot; John C. H. Geisow, Abingdon, both of England

[73] Assignee: British Gas Corporation, London, England

[21] Appl. No.: 620,953

[22] Filed: Jun. 15, 1984

[30] Foreign Application Priority Data

Jun. 17, 1983 [GB] United Kingdom ............... 8316611

[51] Int. Cl.⁴ .................................... G01N 29/04
[52] U.S. Cl. .................................... 73/639
[58] Field of Search ............... 73/639, 641, 635, 638, 73/432 B; 248/231.2, 231.3, 297.2, 316.2; 128/660; 301/125; 16/47, 48; 403/248, 290, 331, 335, 338, 314, 374

[56] References Cited

U.S. PATENT DOCUMENTS

| | | | |
|---|---|---|---|
| 2,049,528 | 8/1936 | Stroud | 52/790 |
| 3,127,020 | 3/1964 | Bibb | 403/290 |
| 3,351,313 | 11/1967 | Guillon | 248/297.2 |
| 3,771,354 | 11/1973 | Miller | 73/641 |

FOREIGN PATENT DOCUMENTS 12803  1/1983  Japan ..................... 16/47

Primary Examiner—Jerry W. Myracle
Assistant Examiner—John E. Chapman, Jr.
Attorney, Agent, or Firm—Watson, Cole, Grindle & Watson

[57] ABSTRACT

A mounting for locating in side-by-side relationship two ultrasonic wheel probes 10 used for ultrasonically inspecting a pipeline, the mounting including a mounting member 12 defining a slide 16, and two slider members 14 located in back-to-back relationship in the slide 16 and retained therein by a backing member 38. Each slider member 14 is adapted to locate one of the wheel probes 10.

6 Claims, 6 Drawing Figures

MOUNTING

FIELD OF THE INVENTION

This invention relates to a mounting for locating two devices in side by side relationship, for example two wheel probes for ultrasonically inspecting a component.

SUMMARY OF THE INVENTION

According to the present invention, there is provided a mounting for locating two ultrasonic wheel probes in side by side relationship, the mounting comprising a mounting member defining a slide therein, the slide being open at one end and closed at the other end, two slide members which each have a slider portion at each side thereof, the two slide members being arranged to locate in back-to-back slidable relationship in the slide, and a backing member arranged to be removably secured to the mounting member so as to close said open end of the slide whereby in use to oppose displacement of the slide members from the slide, each slide member being adapted at an outer face thereof to locate a respective the wheel probe.

Preferably, the slide in the mounting member is defined by grooves in opposing relationship, the slider portions of the slide members defining tongue portions locatable in the grooves.

The slide members at each inner face thereof may have wedge-shaped faces arranged to be in opposing relationship in the slide, and bars of cylindrical form may locate between adjacent said wedge-shaped faces.

Desirably, screw means are provided for urging the bars against the wedge-shaped faces so as to hold the slider portions against the sides of the slide.

Each slide member at said outer face thereof may define an axle for locating a rotatable wheel probe containing an ultrasonic transducer for inspecting a component along which the wheel probe is arranged to run, and the mounting member may be adapted so as to be pivotally supported in a carrier therefor.

The mounting of the invention has one application for locating two wheel probes in a compact side by side assembly, each wheel probe containing an ultrasonic transducer for inspecting a component along which the wheel probes are arranged to run. Each wheel probe may be removed from the mounting without the other which can be an advantage during servicing of the wheel probes and can be readily replaced without the need for extensive alignment checks when in the mounting.

DESCRIPTION OF THE DRAWINGS

The invention will now be further described by way of example only with reference to the accompanying drawings in which.

DETAILED DESCRIPTION OF THE PREFERRED EMBODIMENT

Figure 1:
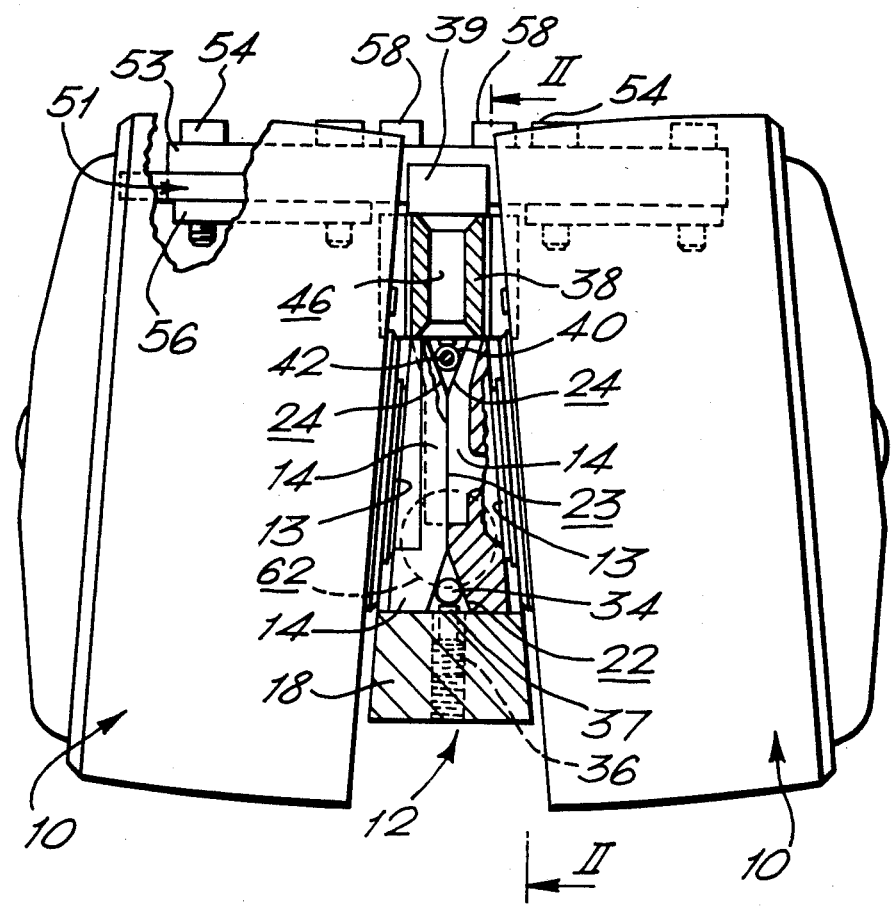
FIG. 1 shows a partly broken away side view of a wheel probe assembly.
Figure 2:
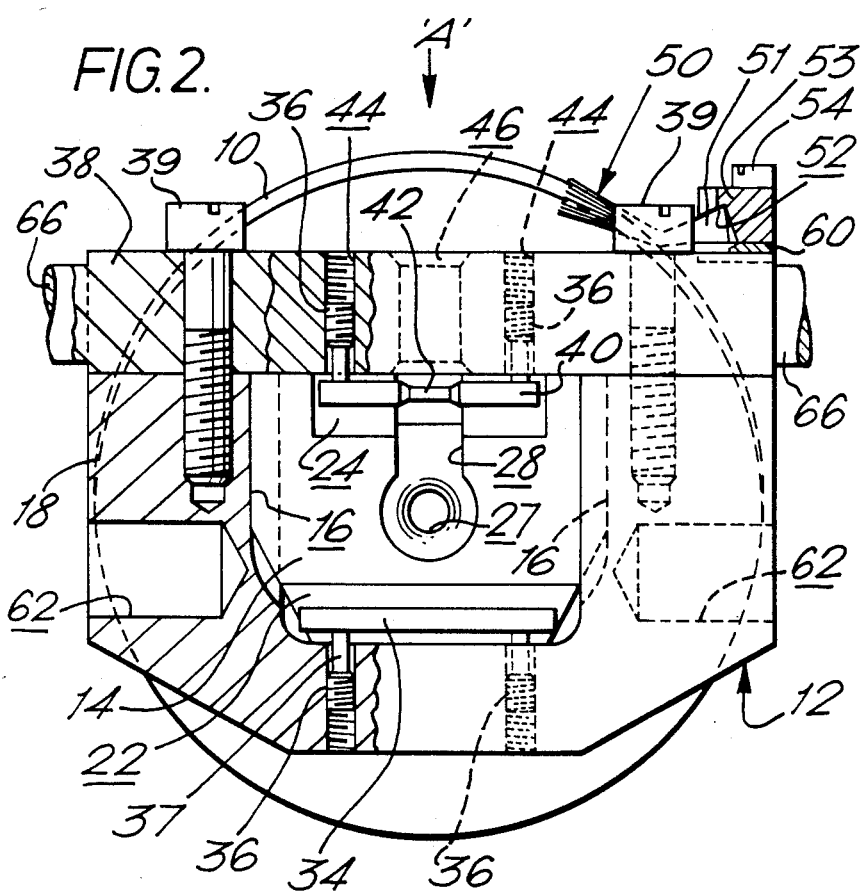
FIG. 2 shows a partly broken away view on the line II—II of FIG. 1.
Figure 3:
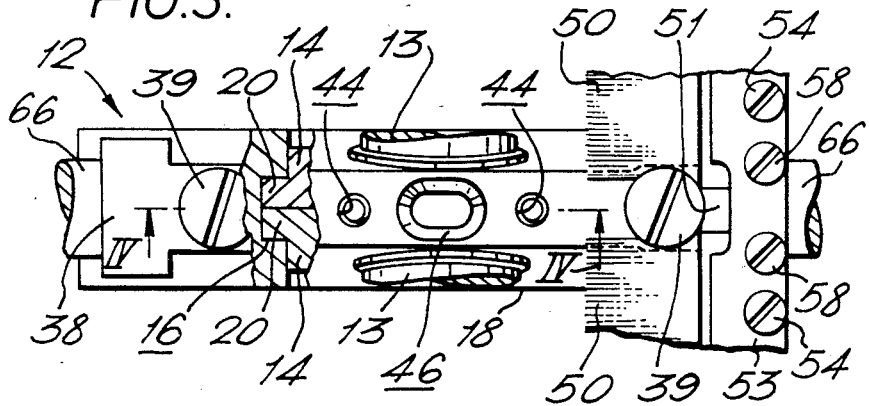
FIG. 3 shows a partly broken away view in the direction of arrow 'A' of FIG. 2.

Referring now to FIGS. 1 to 3, two wheel probes 10 provided with transducers (not shown) for ultrasonically inspecting a wall of a pipeline, are shown locating in a mounting 12. An example of a wheel probe 10 is shown in U.S. Pat. No. 4,302,976, and comprises a hermetically sealed hollow body freely rotatable at one end of a pivotable shaft, and containing two ultrasonic transducers for transmitting ultrasonic signals into a wall of a pipeline along which the hollow body is arranged to run.

Figure 4:
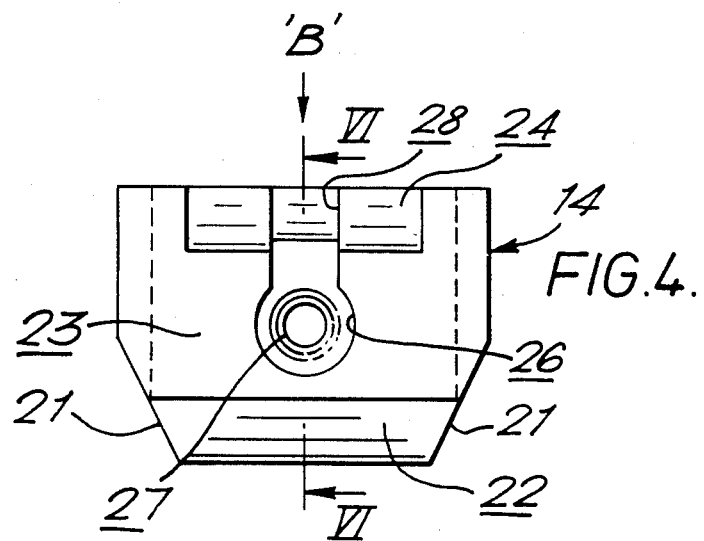
FIG. 4 shows a fragmentary view on the line IV—IV of FIG. 3.
Figure 5:
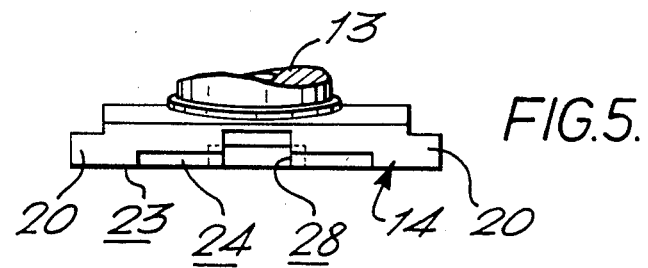
FIG. 5 shows a fragmentary view in the direction of arrow 'B' of FIG. 4.
Figure 6:
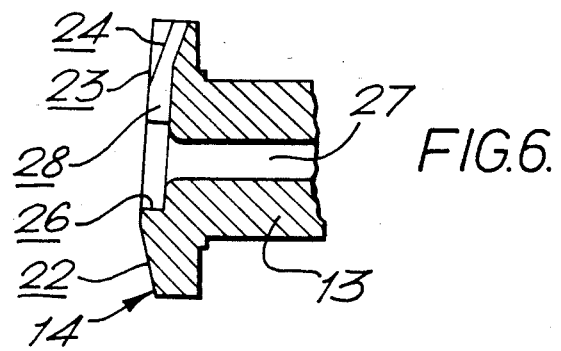
FIG. 6 shows a fragmentary view on the line VI—VI of FIG. 4.

Each wheel probe 10 has a stub axle 13 which terminates in a slide member 14 that locates in a slide in the form of close fitting grooves 16 in a 'U'-shaped steel pivot block 18 of the mounting 12. As shown in FIGS. 4 to 6 from which details of the pivot block 18 have been omitted for clarity, each slide member 14 is shaped at each side to define a tongue 20, and is chamfered at lower corners 21. A lower wedge-shaped face 22 extends across the bottom of an inner face 23 of the slide member 14, and an upper wedge-shaped face 24 extends symmetrically across a top part of the inner face 23. A part-circular recess 26 set in the inner face 23 is aligned with an axial hole 27, and connects with a slot 28 that extends to the upper edge of the slide member 14. A lead (not shown) from the respective wheel probe 10 extends through the hole 27 and the slot 28 for connection to appropriate processing apparatus (not shown).

Referring again to FIGS. 1 to 3, the slide members 14 of two wheel probes 10 with inner faces 23 adjacent locate in the pivot block 18 such that the tongues 20 engage together in the grooves 16. A plain wedge bar 34 is held against the adjacent lower angled faces 22 of the slide members 14 by two screws 36 having spigoted ends 37, so as to force the slide members 14 against a backing bar 38 secured to the pivot block 18 by two screws 39, which backing bar opposes displacement of the slider members 14 from the grooves 16. A wedge bar 40 having a mid-portion 42 of reduced diameter is pressed against the upper wedge-shaped faces 24 by another two screws 36 but located in threaded holes 44 in the backing bar 38. Tightening of the screws 36 secures the slide members 14 firmly in the grooves 16 as the slide members 14 are forced apart by the wedge bars 34, 40 against the sides of the grooves 16. A slot 46 through the backing bar 38 connects with the slots 28 in the slide members 14 to complete a path for the leads from the slots 28. Two wide nylon brushes 50 at each wheel probe 10, have dovetail shaped holders 51 locating in a dovetail recess 52 in a support bar 53, the brushes 50 being secured to the support bar 53 by screws 54 which extend through the support bar 53 and engage a respective locking bar 56. The support bar 53 is secured to the backing bar 38 by two screws 58, a packing piece 60 being inserted between the backing bar 38 and the support bar 53 to adjust the height of the brushes 50 relative to the wheel probes 10. Two oppositely positioned coaxial cylindrical holes 62 in the sides of the pivot block 18 provide locations for respective pivot pins (not shown) to support the pivot block 18 in a carrier such as an inspection vehicle or machine in which the pivot block 18 is to be mounted. An example of such an inspection machine is described in the aforementioned British Patent Specification. The backing bar 38 may also be suitably shaped to provide spigots 66 at each end for location in a guide groove (not shown) in the inspection vehicle.

In use of the wheel probes 10 in the mounting 12, the wheel probes 10 are moved along a component to be inspected, for example the wall of a pipeline. The transducers of the wheel probes 10 are fired to send pulses of ultrasound into the component, and subsequently listen for ultrasonic signals reflected from defects in the component. The mouting 12 is able to pivot about the holes 62 to align the wheel probe 10 with the surface of the component, whilst the spigots 66 can be used to limit this pivotal movement of the wheel probes 10.

The mounting 12 enables the wheel probes 10 to be readily assembled in an inspection vehicle or machine, and allows one of the wheel probes 10 to be removed from the mounting 12 without the other. The mounting 12 also enables a more compact assembly of wheel probes to be provided than hitherto, which should alleviate to some extent problems encountered with local variations of the surface of the component being inspected.

We claim:

1. The combination of two ultrasonic wheel probes and a mounting means for positioning said ultrasonic wheel probes in side-by-side relationship, said mounting means comprising a mounting member defining a slide therein, the slide being open at one end and closed at the other end, two slide members each having a slider portion at opposite sides thereof, the two slide members being arranged to locate in back-to-back slideable relationship in the slide, and a backing member arranged to be removably secured to the mounting member so as to close said open end of the slide whereby in use to oppose displacement of the slide members from the slide, each slide member being adapted at an outer face thereof to locate a respective said wheel probe.

2. The combination as claimed in claim 1, wherein the slide in the mounting member is defined by grooves in opposing relationship, and wherein the slider portions of the slide members define tongue portions locatable in the grooves.

3. The combination as claimed in claim 2, wherein each groove is of rectangular form.

4. The combination as claimed in claim 1 or claim 2, wherein each slide member has an inner face and each inner face has wedge-shaped faces arranged to be in opposing relationship in the slide, and bars of cylindrical form are located between adjacent said wedge-shaped faces.

5. The combination as claimed in claim 4, including screw means for urging the bars against the wedge-shaped faces so as to hold the slider portions against the sides of the slide.

6. The combination as claimed in claim 1, wherein each slide member at said outer face defines an axle for locating a rotatable ultrasonic wheel probe for inspecting a component along which the wheel probe is arranged to run.

* * * * *